US007304300B2

(12) United States Patent
Partin et al.

(10) Patent No.: US 7,304,300 B2
(45) Date of Patent: Dec. 4, 2007

(54) INFRARED TAG AND TRACK TECHNIQUE

(75) Inventors: Judy K. Partin, Idaho Falls, ID (US); Mark L. Stone, Idaho Falls, ID (US); John Slater, Albuquerque, NM (US); James R. Davidson, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 311 days.

(21) Appl. No.: 11/082,030

(22) Filed: Mar. 15, 2005

(65) Prior Publication Data

US 2007/0158593 A1 Jul. 12, 2007

(51) Int. Cl.
*G01P 5/20* (2006.01)

(52) U.S. Cl. .................. 250/302; 250/408.1; 376/157; 358/1.9; 436/27

(58) Field of Classification Search ................. 250/302
See application file for complete search history.

(56) References Cited

U.S. PATENT DOCUMENTS

| | | | |
|---|---|---|---|
| 4,269,784 A * | 5/1981 | Doyle | 518/715 |
| 4,390,452 A * | 6/1983 | Stevens | 252/408.1 |
| 5,643,764 A * | 7/1997 | Kosak et al. | 435/91.1 |
| 5,786,218 A * | 7/1998 | Pivonka et al. | 436/34 |
| 7,057,177 B2 * | 6/2006 | Davis et al. | 250/341.8 |
| 2005/0175931 A1 * | 8/2005 | Barr et al. | 430/270.1 |

* cited by examiner

*Primary Examiner*—Nikita Wells
*Assistant Examiner*—Phillip A. Johnston
(74) *Attorney, Agent, or Firm*—Wells St. John P.S.

(57) ABSTRACT

A method of covertly tagging an object for later tracking includes providing a material capable of at least one of being applied to the object and being included in the object, which material includes deuterium; and performing at least one of applying the material to the object and including the material in the object in a manner in which in the appearance of the object is not changed, to the naked eye.

31 Claims, 14 Drawing Sheets

START

PROVIDE A POLYMER MATERIAL INCLUDING DEUTERATED HYDROGEN — 66

COVERTLY APPLY THE MATERIAL TO AN OBJECT — 68

DETECT THE MATERIAL USING AN INFRARED CAMERA — 70

STOP

INFRARED SPECTRA OF REGULAR AND DEUTERATED POLYSTYRENE
REGULAR POLYSTYRENE
DEUTERATED POLYSTYRENE
20
22
0
2
4
6
8
10
12
14
16
18
20
MICRONS

INFRARED SPECTRA OF REGULAR AND DEUTERATED
POLY (methyl methacrylate)
REGULAR PMMA
DEUTERATED PMMA
24
26
0
2
4
6
8
10
12
14
16
18
20
MICRONS 72
74

INFRARED TAG AND TRACK TECHNIQUE

GOVERNMENT RIGHTS

The United States Government has certain rights in this invention pursuant to Contract No. DE-AC07-99ID13727, and Contract No. DE-AC07-05ID14517 between the United States Department of Energy and Battelle Energy Alliance, LLC.

TECHNICAL FIELD

The invention relates to materials and methods of and apparatus for tagging or marking objects. The invention also relates to methods of and apparatus for tracking movement of objects.

BACKGROUND OF THE INVENTION

It is sometimes desirable to covertly track the movement of objects. For example, it may be desirable to catch smugglers or prevent export of export-controlled components.

Some materials used as taggants are generally fluorescent-based and must be illuminated with particular wavelengths and intensities of light to be effectively detected. These materials may not be compatible with use on some substrates, since the substrate itself may fluorescence and interfere with the emission from the taggant. They most commonly produce visible signatures. This limits the ability to covertly tag and identify the objects.

Other types of tags are electronically activated, like the ones commonly found in retail stores. These types of tags are effective, but can not be easily implemented in a covert fashion, nor read out from a distance.

What is needed is a method and apparatus for covertly marking objects. Also needed is a method and apparatus for covertly tracking the movement of objects.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Aspects of the invention provide methods and apparatus for covert tagging of objects. Aspects of the invention provide methods and apparatus for covert tracking of objects. In some aspects, tagged objects may be detected with a filtered, infrared video-compatible camera system under ambient lighting conditions. In some aspects, the camera system is portable and could be carried and used by an individual, or mounted on fixed or moving platforms.

In some embodiments, the tagging involves the substitution of deuterium for hydrogen in commonly available materials. Such materials include waxes, plastics, and paints, for example. Deuterated materials can be produced for the purpose of tagging or can be purchased commercially.

In some embodiments, the material is applied or included in the object to be tracked. A surface of the object could be partially or completely coated with the material. The material can be applied as a wax, or paint, or can be included as a plastic component. In some embodiments, the material is sprayed on an object (e.g., in a spot). Other methods of applying or including the material in the object to be tracked could be employed.

The replacement of most of the hydrogen with deuterium, in a material to be used for tagging an object, results in a very strong spectroscopic signature of the deuterium, even from a very thin layer of wax coating on the surface of the object, such as a cargo container or automobile. This infrared spectroscopic signal can readily be detected with infrared sensitive arrays while the chemical properties of the tagged object, and its visual appearance, remain unchanged.

Figure 1:
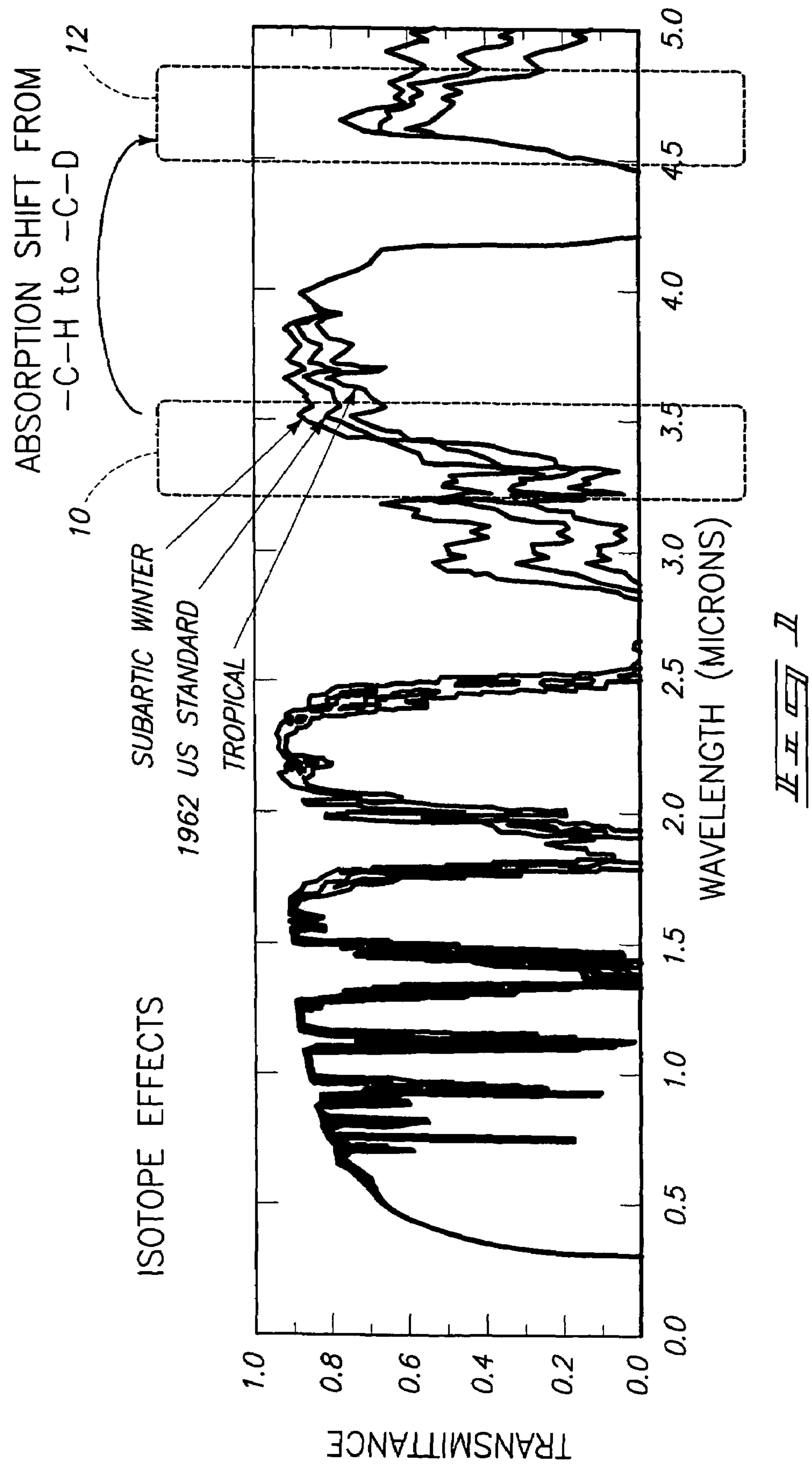
FIG. 1 is a graph of typical atmospheric transmittance versus wavelength showing the regions of absorption due to $H_2O$ and $CO_2$ in the atmosphere. Superimposed are regions where absorption bands (10 and 12) for —C—H and —C—D bonds occur.

In some embodiments, the materials used for tagging are commonly used materials, i.e. waxes, plastics, or clear spray-on materials that would not cause undue suspicion when applied. In the preferred embodiments, the material used as a tag produces a strong spectroscopic signature using a thin layer of material that is not visually noticeable. In these embodiments, the signal can be detected under ambient light using a handheld infrared video camera system. In addition, the spectroscopic change occurs in a region of the electromagnetic spectrum that is readily transmitted through the atmosphere, allowing for the possibility of remote detection over large distances. For example, FIG. 1 illustrates the difference in absorption signatures when changing from —C—H bonds (see portion 10 of the graph) to —C—D bonds (see portion 12 of the graph).

In some embodiments, multiple different kinds of deuterated polymers could be employed, each having different signatures. This allows, for example, certain tracked objects to be distinguished from each other.

These materials are used to covertly mark and track a variety of objects under a number of operational scenarios, in alternative embodiments. For example, a small plastic section of a sensitive, export-controlled component is treated and imaged by a camera system located in a ceiling or other unobtrusive location, in some embodiments. Sections of large objectives, such as a cargo container are fabricated with taggent-dopped plastic and remotely tracked by an individual in a toll booth or standing by the side of the road, in other embodiments. Vehicles, such as cars or trucks, are coated with a thin layer of wax and observed from overhead platforms such as aircraft, helicopters, bridge overpasses, or tall buildings, in other embodiments.

In some embodiments, this technology is used to help government agencies and industrial firms in tracking sensitive items ranging from computer components to vehicles.

In some embodiments, the tagged material is one in which hydrogen atoms have been replaced with deuterium. Other isotopes could also be employed, in alternative embodiments. Common materials can be manufactured with deuterated hydrogen, or coated with a deuterated wax or paint. Many of the materials of interest, for example the wax n-dotriacontone, are commercially available in fully deuterated form. The polymer polyethylene, a thermally formable plastic, is also available in a fully deuterated form. For nonthermal plastics, that is those which must be made in final form, many of the monomers used as starting materials are also available in deuterated forms. Both latex and oil based paints can be prepared in deuterated form.

In spite of the relative ease which common materials could be produced, no high levels of deuteration are found in any commercial products because of the cost. Typically, deuterated hydrocarbons cost around $400 per gram (for most applications of embodiments of the invention, only the surface layer is important so the cost of materials should not be prohibitive).

Thousands of deuterated materials are available. Typical applications include nuclear magnetic resonance, or for use as solvents. However, there are not many deuterated polymers that are commercially available. In some embodiments, a deuterated polymer is used to tag an object. While it is possible to make substantially any polymer a deuterated polymer, there are not many deuterated polymers available. This is because it would be expensive to make parts out of deuterated polymers that are presently made out of regular polymers. However, in some embodiments of the invention, entire objects are not made out of a deuterated polymer, only parts of the object are made out of a deuterated polymer, or a deuterated polymer is used as a coating or even as a small marking. In alternative embodiments, whole parts of smaller objects may be made out of a deuterated polymer, such as mobile phone cases or keypads, or individual keys in a computer keyboard, for example.

High levels of deuteration do not occur naturally so there is little possibility of false positive identification using this technique.

Figure 2:
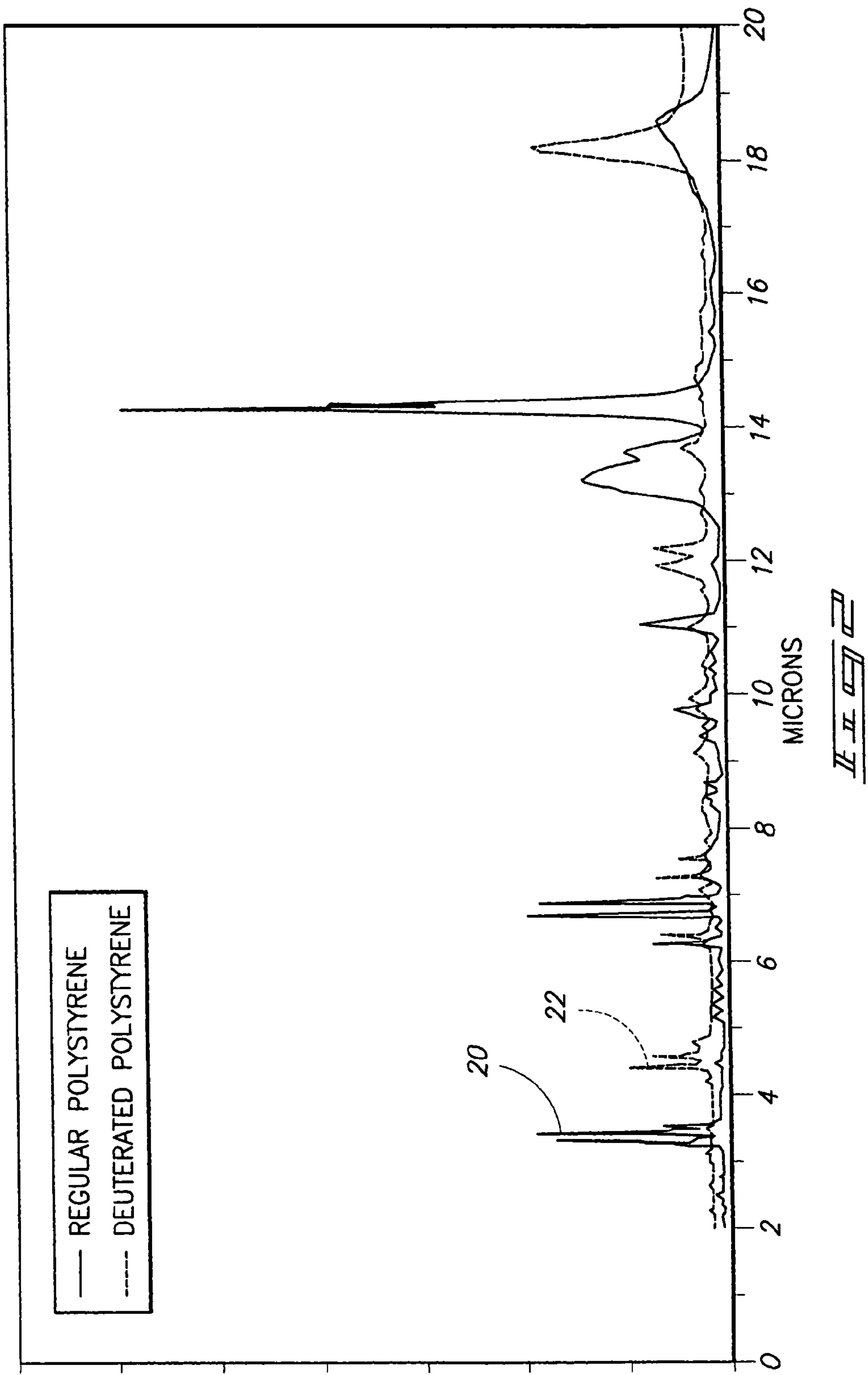
FIG. 2 is a graph of absorbance versus wavelength for regular polystyrene and deuterated polystyrene.

An example of a deuterated polymer that is employed, in some embodiments of the invention, is deuterated polystyrene. FIG. 2 shows the absorption difference or shift between regular polystyrene (see plot 20) and deuterated polystyrene (see plot 22 and spike between 4 and 5 microns). The absorption signature can be used to detect the deuterated material, making the material effective as a tag.

Figure 3:
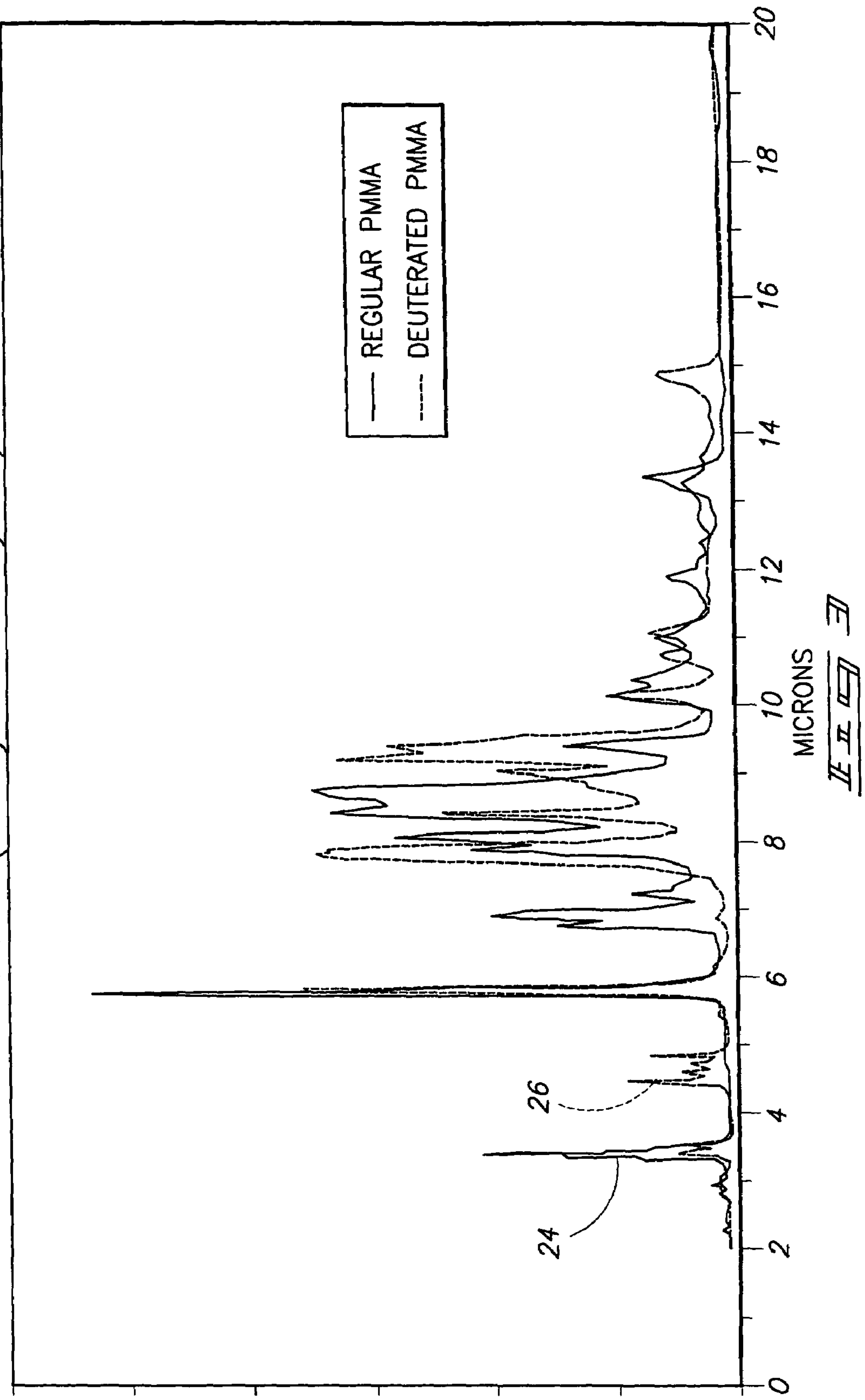
FIG. 3 is a graph of absorbance versus wavelength for regular poly(methyl methacrylate) and deuterated poly(methyl methacrylate).

An example of a deuterated polymer that is employed, in other embodiments of the invention, is deuterated poly (methyl methacrylate). FIG. 3 shows the absorption difference between regular poly(methyl methacrylate) (see plot 24) and deuterated poly(methyl methacrylate) (see plot 26 and spike between 4 and 5 microns).

Figure 4:
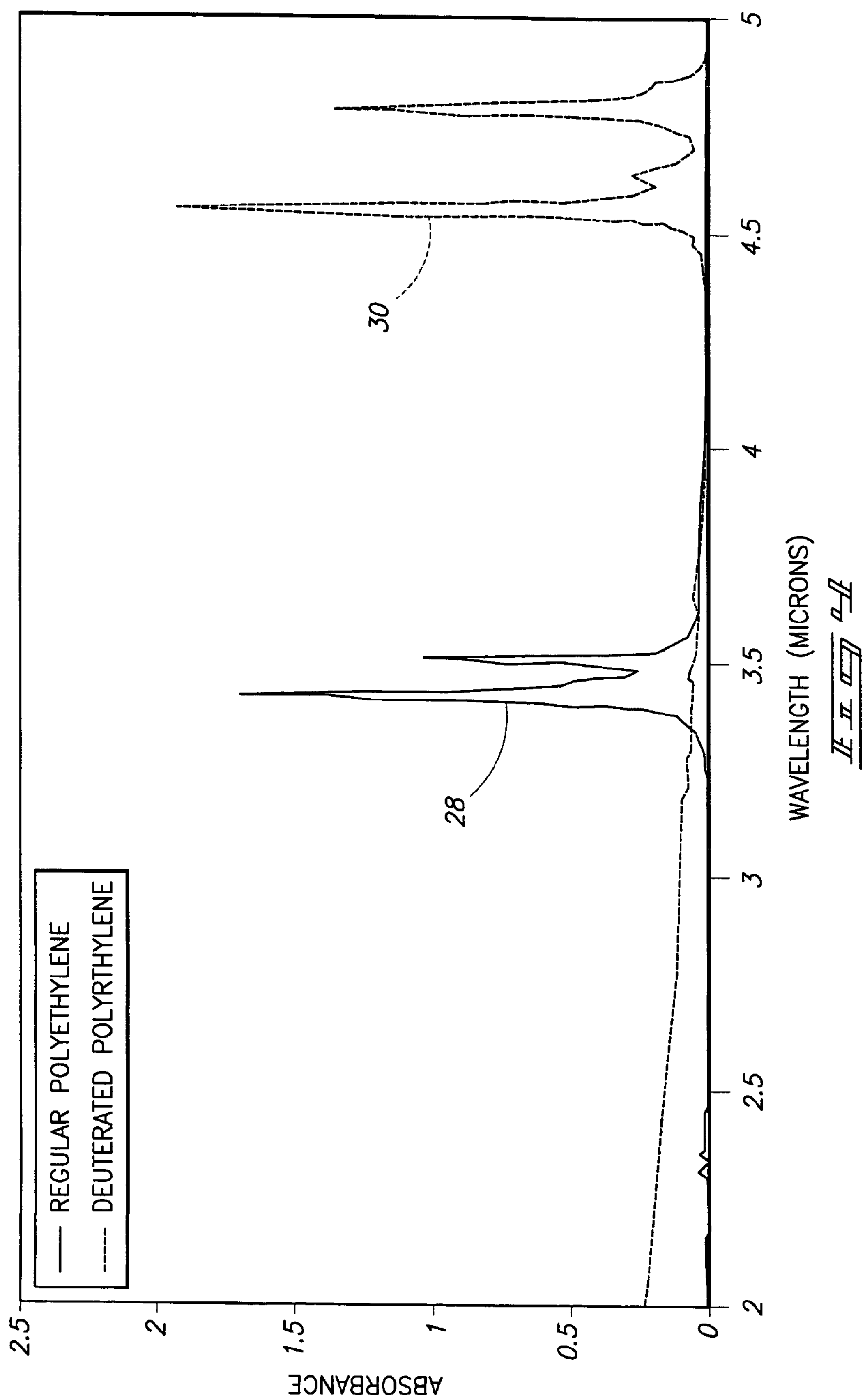
FIG. 4 is a graph of absorbance versus wavelength for regular polyethylene and deuterated polyethylene.

Another example of a deuterated polymer that is employed, in some embodiments of the invention, is deuterated polyethylene. FIG. 4 shows the absorption difference between regular polyethylene (see plot 28) and deuterated polyethylene (see plot 30).

Figure 5:
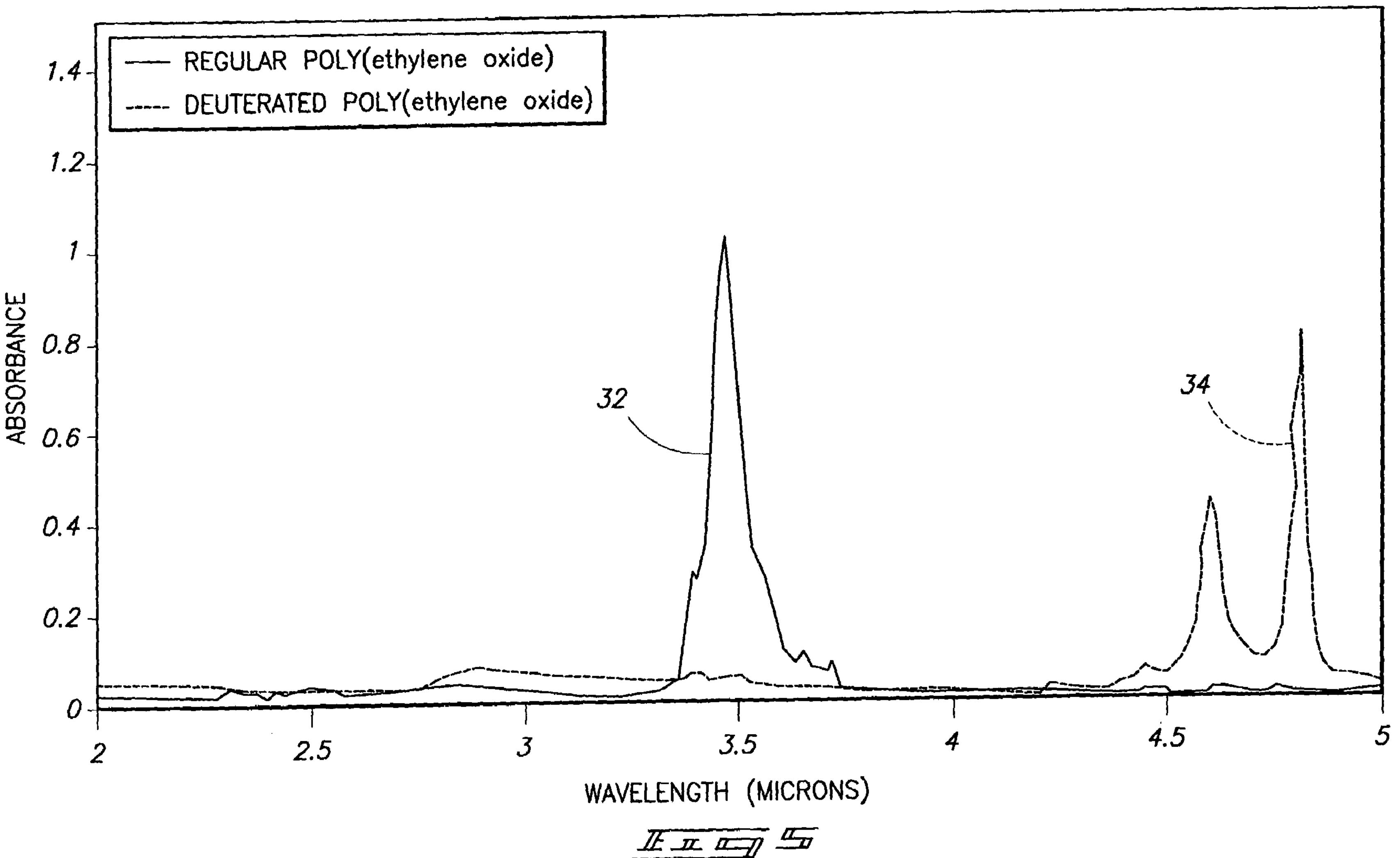
FIG. 5 is a graph of absorbance versus wavelength for regular poly(ethylene oxide) and deuterated poly(ethylene oxide).

Another example of a deuterated polymer that is employed, in some embodiments of the invention, is deuterated poly(ethylene oxide). FIG. 5 shows the absorption difference between regular poly(ethylene oxide) (see plot 32) and deuterated poly(ethylene oxide) (see plot 34).

Figure 6:
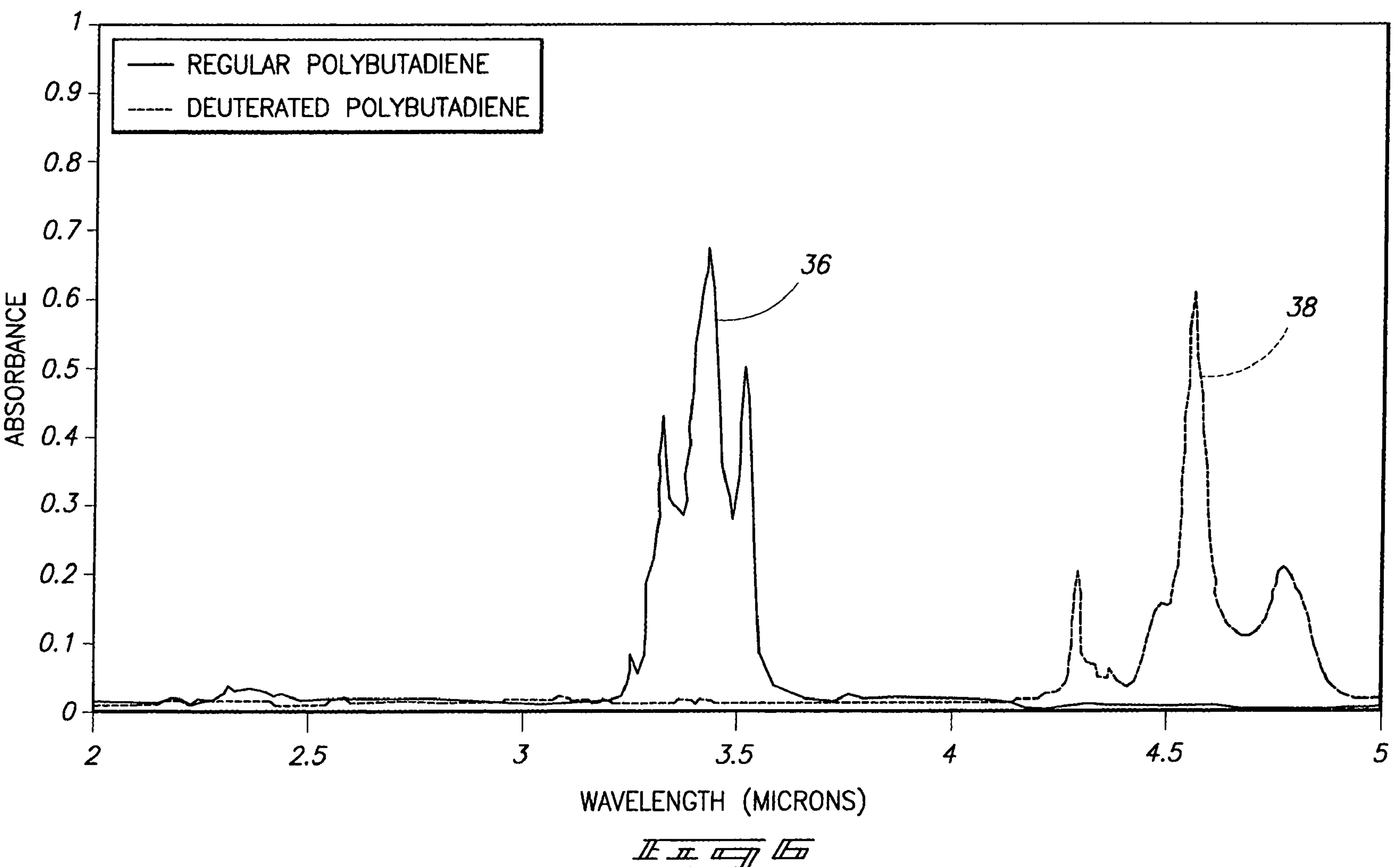
FIG. 6 is a graph of absorbance versus wavelength for regular polybutadiene and deuterated polybutadiene.

Another example of a deuterated polymer that is employed, in some embodiments of the invention, is deuterated polybutadiene. FIG. 6 shows the absorption difference between regular polybutadiene (see plot 36) and deuterated polybutadiene (see plot 38).

Figure 7:
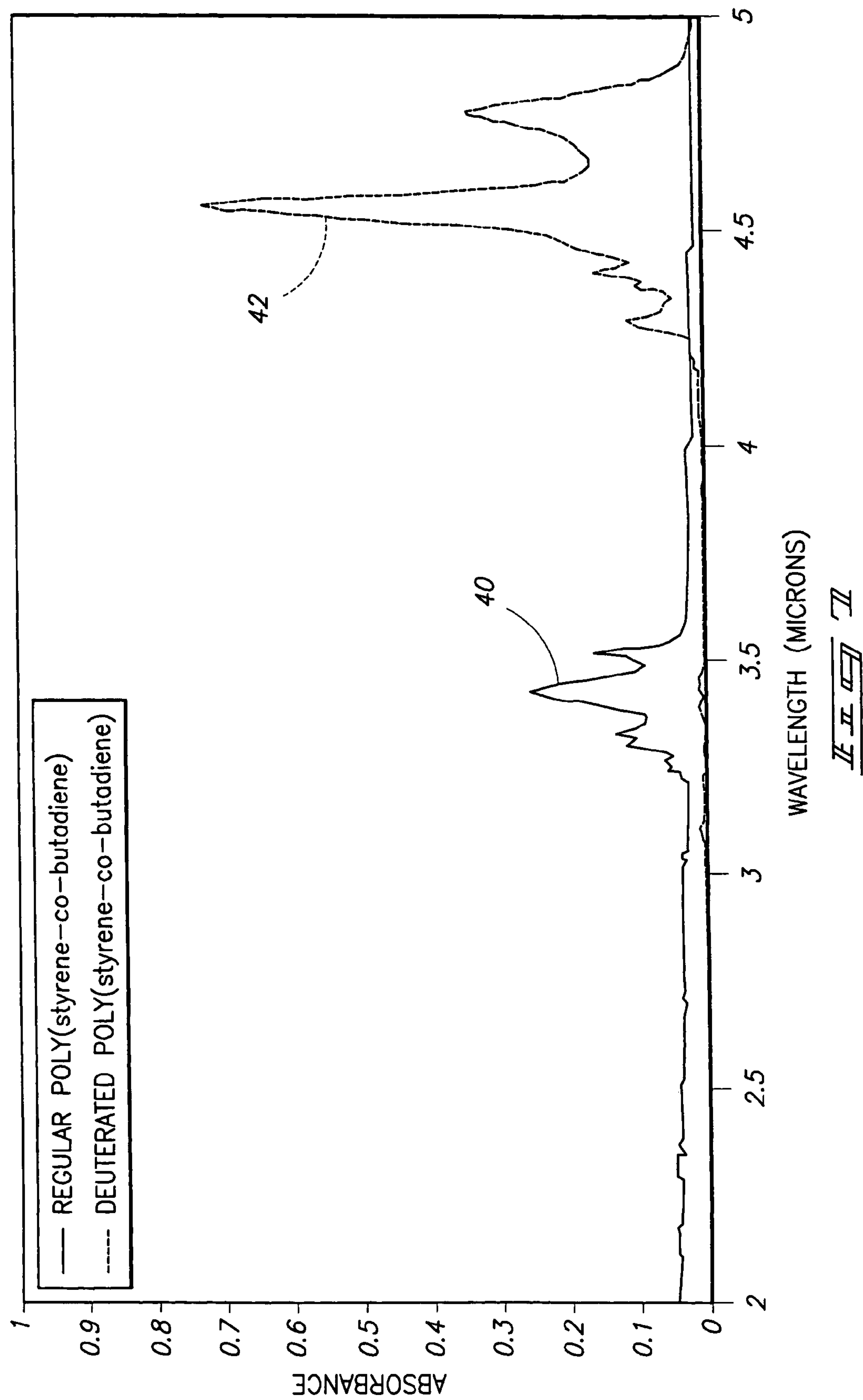
FIG. 7 is a graph of absorbance versus wavelength for regular poly(styrene-co-butadiene) and deuterated poly(styrene-co-butadiene).

Another example of a deuterated polymer that is employed, in some embodiments of the invention, is deuterated poly(styrene-co-butadiene). FIG. 7 shows the absorption difference between regular poly(styrene-co-butadiene) (see plot 40) and deuterated poly(styrene-co-butadiene) (see plot 42).

Figure 8:
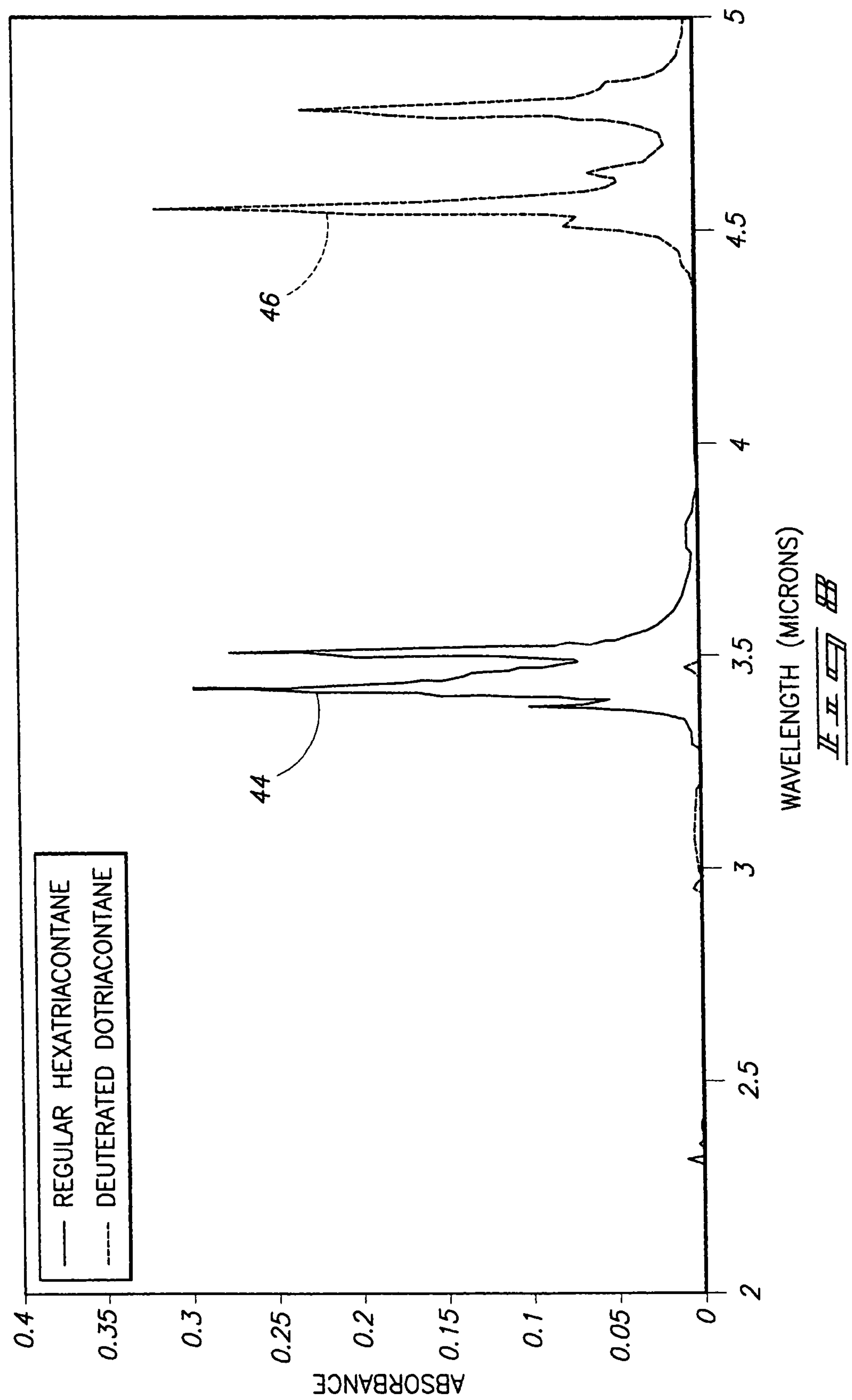
FIG. 8 is a graph of absorbance versus wavelength for hexatriacontane and dotriacontane.

Another example of a deuterated polymer that is employed, in some embodiments of the invention, is deuterated dotriacontane. FIG. 8 shows the absorption difference between hexatriacontane (see plot 44) and dotriacontane (see plot 46).

Figure 9:
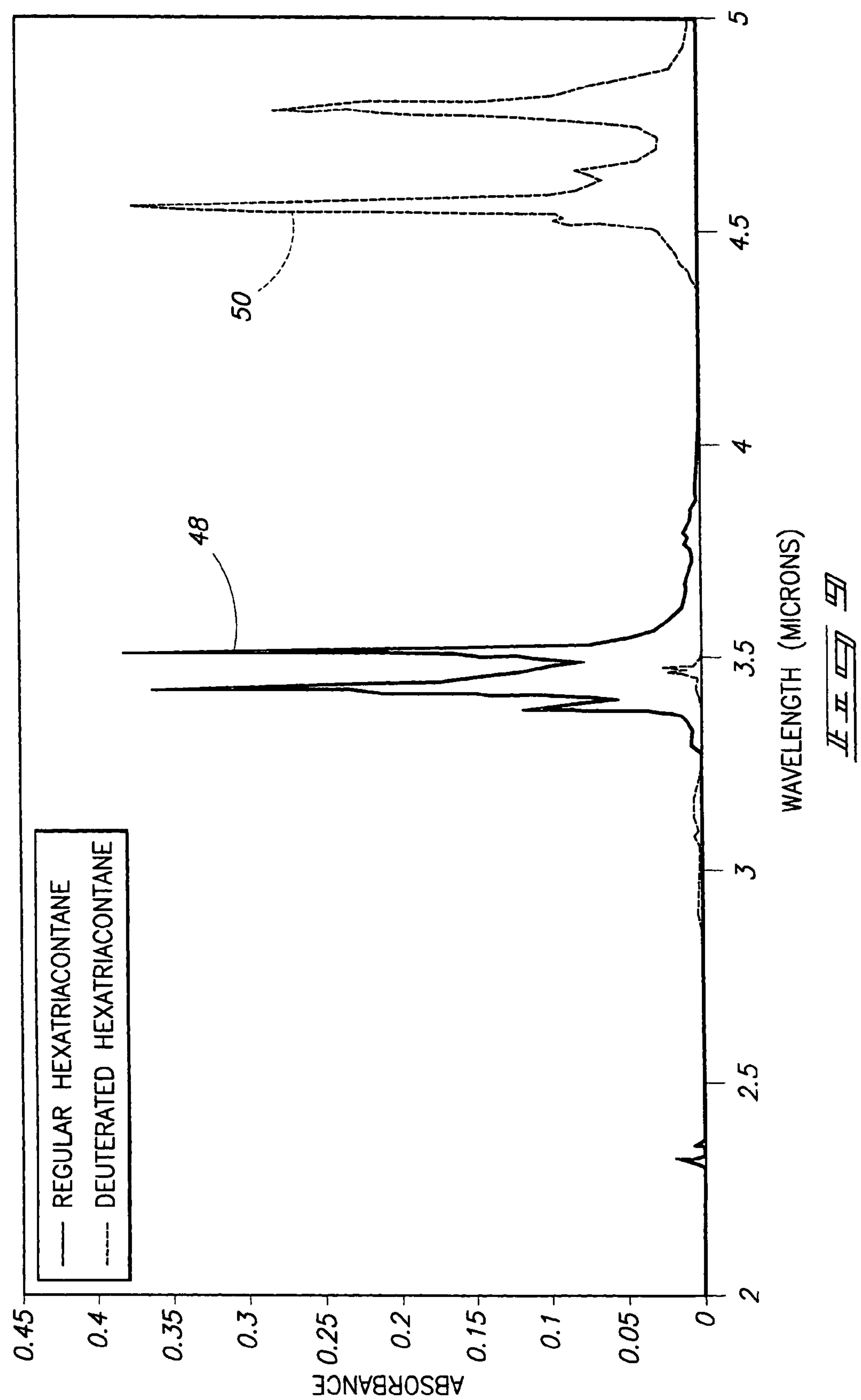
FIG. 9 is a graph of absorbance versus wavelength for regular hexatriacontane and deuterated hexatriacontane.

Another example of a deuterated polymer that is employed, in some embodiments of the invention, is deuterated hexatriacontane. FIG. 9 shows the absorption difference between regular hexatriacontane (see plot 48) and deuterated hexatriacontane (see plot 50).

Thus, some embodiments are based upon the infrared absorption frequency shift associated with changing C—H to C—D bonds. C—H absorption occurs in approximately the 3.2 to 3.5 micron range. On the other hand, C—D absorption occurs in approximately the 4.4 to 4.7 micron range.

In some preferred embodiments, a material is selected having strong absorptions in the 4.6 to 4.8 micron range. This is because there is a spectral window in this area for transmission through air. Thus, materials in this region would have lower interferences from water and $CO_2$.

In alternative embodiments, a material is selected having absorption in the 3.8 to 4.2 micron range. This range of the atmospheric absorption spectrum is even less prone to interference. The inventors have determined that replacing the hydrogens with deuteriums in alcohols and amines will produce absorptions in the desired region. More particularly, O—H and N—H absorptions occur in approximately the 2.9 to 3.0 micron range. On the other hand, O—D and N—D absorptions occur in approximately the 3.9 to 4.1 micron range.

Figure 14:
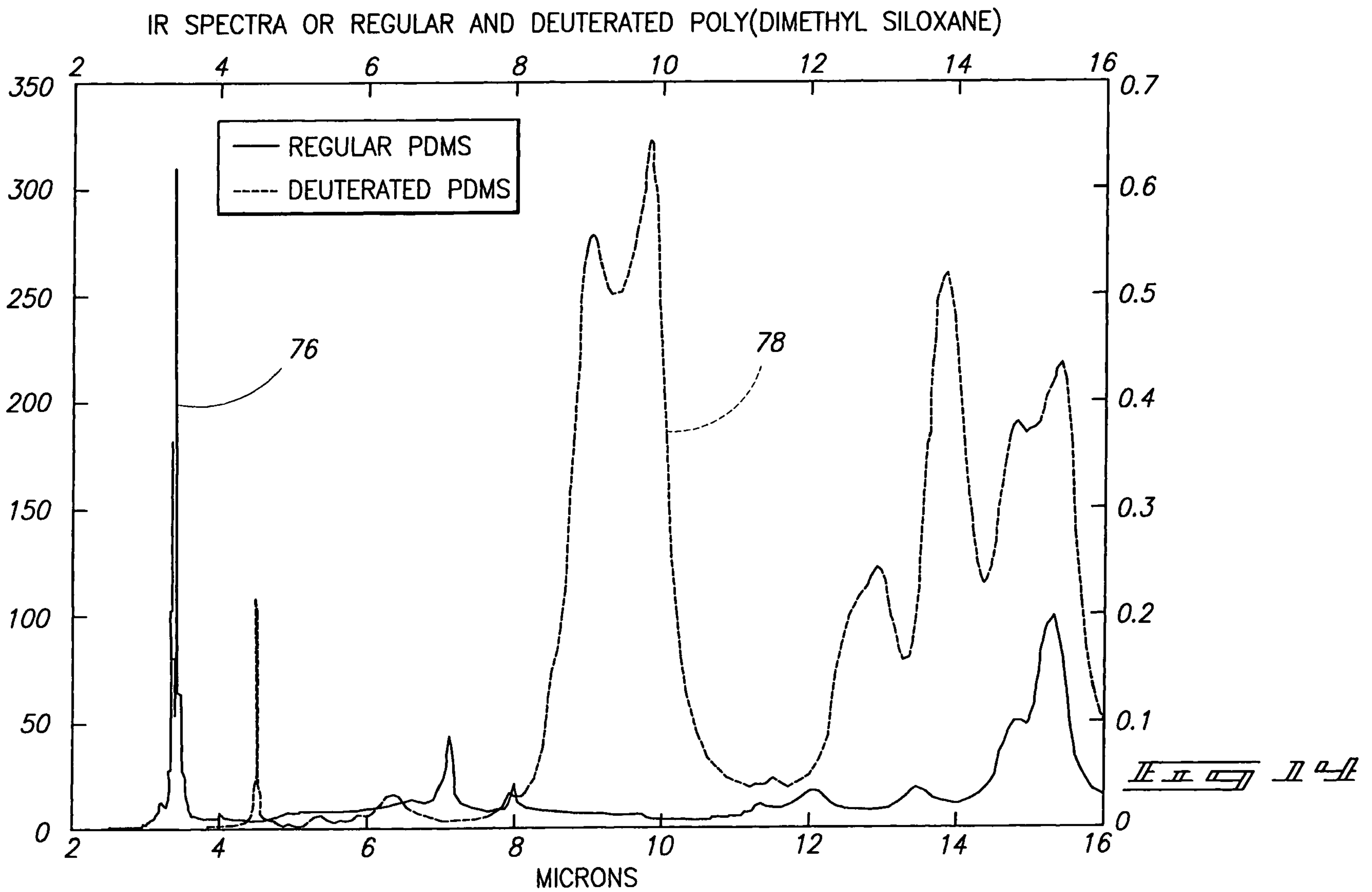
FIG. 14 is a graph of absorbance versus wavelength for regular Poly(dimethyl siloxane) and deuterated Poly(dimethyl siloxane).

In alternative embodiments, a material is selected having absorption in the 8 to 14 micron range or, more particularly, in the 8 to 10 micron range. Other ranges are possible. For example, a deuterated polymer that is employed, in some embodiments of the invention, is deuterated PDMS. FIG. 14 shows the absorption difference between regular PDMS (see plot 76) and deuterated PDMS (see plot 78). FIG. 14 also illustrates that there are useful isotopic shifts that occur in various parts of the spectrum, and that the invention is not limited to materials having absorption in the 3-5 micron range. Other embodiments are possible.

With all of the above, a drastic change or shift in absorption profiles can be seen. The signature of the deuterated polymer is readily detected by a detector, which will be described below in greater detail.

More particularly, when a fully deuterated surface is examined spectroscopically, all the vibrational features corresponding to the carbon-hydrogen stretching will be shifted in frequency by roughly 40 percent to lower frequencies, as dictated by Hooke's law which relates frequency to mass. This is a very large shift and is easily detectable using a properly designed observation system, even though the chemical and physical properties of the materials are unchanged. The deuteration of a material produces a very strong absorption in the 3.5-4.5 micron region of the electromagnetic spectrum. The absorbance of a fully deuterated compound is strong enough to reduce the intensity of an impinging light propagating through the compound to around 5% its initial strength within a 100 micron thick layer of material, depending on the wavelength. This substantially affects light emitted by or reflected from the material.

Figure 10:
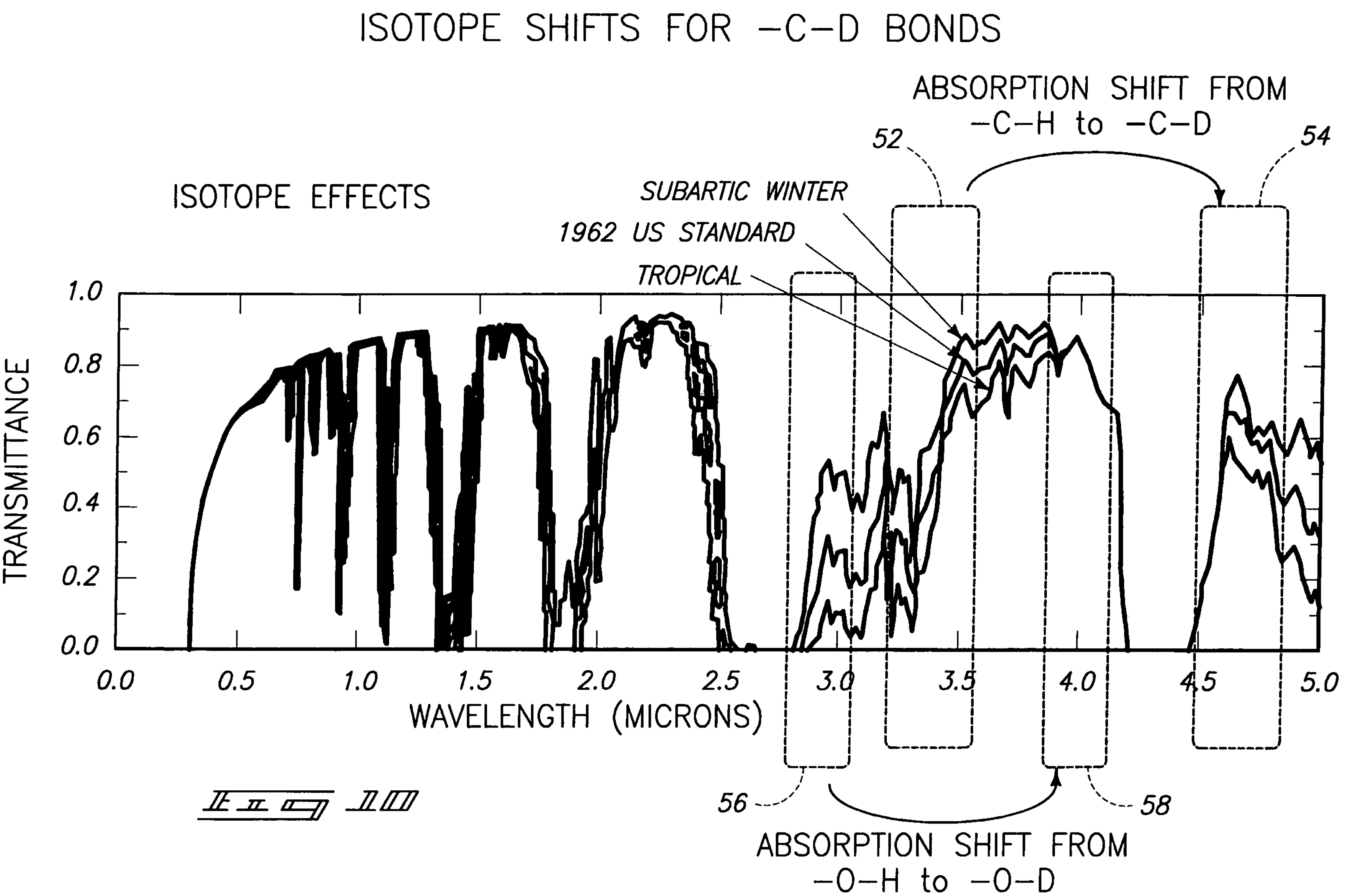
FIG. 10 is a graph of transmittance versus wavelength showing absorption shifts from —O—H bonds to —O—D bonds and from —C—H bonds to —C—D bonds.

There are a lot of different types of carbon-hydrogen bonds and additional isotopes that could be investigated. Additionally, other classes of materials for which isotope shifts could be advantageously employed include alcohols. FIG. 10 illustrates that there is not only a readily discernable absorption shift when changing —C—H bonds (see portion 52 of the graph) to —C—D bonds (see portion 54 of the graph) but also when changing —O—H bonds (see portion 56 of the graph) to —O—D bonds (see portion 58 of the graph).

To better enable one of ordinary skill in the art to make and use the invention, some commercially available deuterated materials will now be provided. There are several companies worldwide that commercially produce deuterated materials that are employed in various embodiments. Some of these sell mostly deuterated polymers, others sell deuterated chemicals (that could be used as starting materials), and some sell a mixture of deuterated polymers and deuterated chemicals that could be used as starting materials. These companies include, for example:

1. Aldrich Chemical Company, Milwaukee, Wis.

2. Polymer Source, Inc., Quebec, Canada

3. CDN Isotopes Inc., Quebec Canada

4. Cambridge Isotopes Laboratories, Inc., Andover, Mass., and

5. Icon Isotopes, Summit, N.J.

The following selected list is representative of the types of polymers that are commercially available.

Deuterated Homopolymers

Deuterated Polyacrylonitrile (d3)

Deuterated Poly(alkyl acrylate)

Deuterated Poly(acrylic acid) (d3)

Deuterated Poly(n-butyl acrylate) (d9)

Deuterated Poly(ethyl acrylate) (d5)

Deuterated Poly(methyl acrylate) (d3)

Deuterated Poly(alkyl methacrylate)

Deuterated Poly(t-butyl methacrylate) (d14)

Deuterated Poly(ethyl methacrylate) (d5)

Deuterated Poly(methacrylic acid) (d5)

Deuterated Poly(methyl methacrylate) (d8)

Deuterated Poly(methyl methacrylate) (d5)

Deuterated Poly(methyl methacrylate) (d3-ester)

Deuterated Poly(methyl methacrylate) (d3-a-methyl)

Deuterated Polybutadiene (1,4 addition)

Deuterated α,ω-dihydroxy Terminated Poly(propylene glycol)

Deuterated Polydimethylsiloxane

Deuterated Polyethylene

Deuterated Poly(ethylene oxide)

Deuterated α,ω-dimethoxy Terminated Poly(ethylene oxide)

Deuterated Poly(N-isopropyl acrylamide) (d7)

Deuterated Polyisoprene

Deuterated Poly(styrene sulfonic acid)

Deuterated Polystyrenes

Deuterated Poly(4-methyl (d3) styrene)

Deuterated Poly(4-methoxy styrene (d3))

Deuterated Polystyrene (d8)

Deuterated Polystyrene (d5)

Deuterated Polystyrene (d3)

Deuterated Polystyrene (d2)

Deuterated oligomer of styrene-dimmer (d2)

Deuterated Polystyrene (d1)

Deuterated Poly(4-vinyl (d3) phenol)

Deuterated Poly(2-vinyl pyridine)

Deuterated Poly(2-vinyl-N-methylpyridinium iodide)

Deuterated Condensation Polymers

Deuterated Bisphenol A based Poly(hydroxy ether) (d19)

Deuterated Bisphenol A based Poly(hydroxy ether) (d11)

Deuterated Bisphenol A based Poly(hydroxy ether) (d5)

Deuterated Polycarbonate (d14)

Deuterated Polycarbonate (d8)

Deuterated Polycarbonate (d6)

Deuterated Polycarbonate (d4)

Deuterated Poly(ethylene (d4) terephthalate)

Deuterated Poly(ethylene terephthalate (d4))

Deuterated Polysulfone (d6)

Deuterated Poly(sulfone ether) (d8)

There is an innumerable variety of deuterium labeled chemical species, and many of these can be employed in alternative embodiments. Some embodiments are polymeric species including a couple of oligomer waxes. There are also a large number of copolymers that could also be employed in alternative embodiments. Taking into account these aspects and looking for commercially available materials, a list of commercially available candidates was compiled. The inventors examined the IR spectra of the selected list and after closely examining them, selected preferred materials. Of course, other materials having an absorption shift could be employed as described above and, in some embodiments, the tagging material could be manufactured instead of being obtained commercially. As particular examples, four homopolymers that have a wide cross-section of physical properties and one copolymer that is made from two of the homopolymers already selected were chosen as being materials that are readily employed as well as being commercially available:

1. Polystyrene-d8 (PSTY), Purchased from CDN Isotopes, Product Number D-5486, Average Molecular weight 1,700,000, 98 atom % D, Lot No. T151P2;

2. Poly(methyl methacrylate-d8) (PMMA), Purchased from CDN Isotopes, Product Number D-5451, 98 atom % D, Lot No. S230P1;

3. Poly(ethylene-d4) (PE), Purchased from CDN Isotopes, Product Number D-775, 99.8 atom % D, Lot No. F129BP9;

4. Deuterated 1,2-addition Polybutadiene-d6 (PBUT), Purchased from Polymer Source, Inc., Sample No. P2377-dPBd, Mn=68000, Mw—71500, Mw/Mn=1.05 and 5. Deuterated Poly(butadiene(d6)-co-styrene(d8)) (SBR rubber), Purchased from Polymer Source, Inc., Sample No. P1559-dBd-dSt (dSBR), Mn=60000, Mw/Mn=1.07.

Polystyrene is a clear rigid material commonly seen as the clear beverage cups on airplanes. Poly(methyl methacrylate) is Plexiglas™. Polyethylene is what milk bottles are made from. Polybutadienes are rubbers. The copolymer SBR is a tough rubber used in making tire treads. All of these materials should be solvent castable and/or thermally formable and they clearly are widely different in physical, mechanical, and thermal properties. The material used may be selected, for example, depending on the properties desired for a particular application.

In some embodiments, materials containing O—H, O—D, N—H or N—D are employed. While other embodiments are possible, four families of compounds are believed to be particularly useful for covert tagging and tracking:

1. Poly(vinyl alcohol) (PVAL) and its derivatives. PVAL is water soluble. It is formed by an acid or base catalyzed reaction with the acetate analog in which an H replaces the acetate. Millions of pounds are used annually. If borax is added to a solution of PVAL it crosslinks to form slime. Performing the above reaction in deuterated water and using a deuterated catalyst can make the deuterium analog.

2. Polyacrylamide and its derivatives. This material is the prime constituent in wood glue. When properly crosslinked this material is silly putty. Another crosslinked form is used in agriculture and horticulture applications. It swells several hundred percent and is used to enhance water storage in the ground and potted plants.

3. Nylon or other nitrogen containing polymers.

4. Cellulose and its many, many derivatives. Paper, cardboard, films, and many other products.

Figure 11:
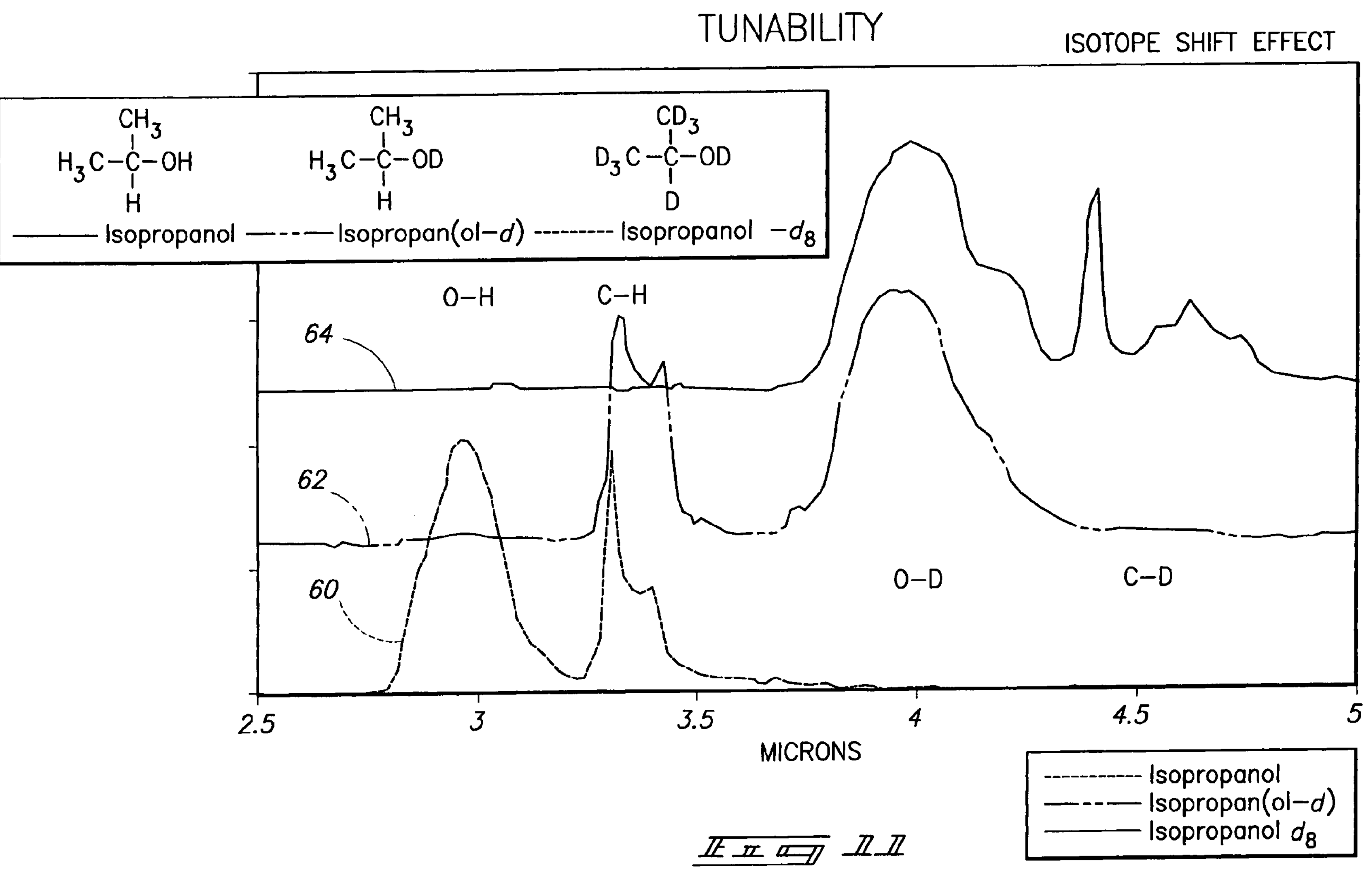
FIG. 11 is a graph of absorbance versus wavelength illustrating peak shifts when deuteriums are substituted for hydrogens.

In some embodiments, isotopes of materials that include both C—H and O—H bonds are employed. Isopropanol is a good example because it contains both C—H and O—H bonds. FIG. 11 illustrates the peak shifts when the deuteriums for hydrogen substitutions are made. Going from trace 60 to 62, the O—H was replaced by O—D. The C—H region remains generally fixed and the O—D shifts from about 2.9 to about 4 microns. Then if the C—H's are replaced by C—D's the shift is seen in the trace 64 at about 4.5 microns.

Two sources of radiation are available for use within the (for example) 3-5 micron band. They include thermal emission from the object, that is the radiation emitted by a blackbody object at 300 K (ambient temperature), and reflected sunlight. The blackbody emission in the 3-5 band is on the order of 600 microwatts per centimeter squared, and the solar radiation is on the order of 2400 microwatts per centimeter squared. Alternatively, in some cases, active illumination is employed, such as by a laser. These sources will allow spectroscopic measurements of the deuterated materials to be performed under a variety of conditions. The 3-5 micron region fortunately lies within an atmospheric window of transparency so that measurements can be performed at a distance. As described above, however, other micron regions can also be employed.

In some embodiments, infrared cameras are used which will allow video images to be collected of the spectroscopically-modified object. These cameras use relatively high resolution (640×480) indium antimonide and platinum silicide focal plane arrays with sensitivity in the 1.5 to 6 micron region of the spectrum. Mercury cadmium telluride has sensitivity in the 8-14 micron range. These systems can detect temperature differences as small as 0.025 degrees C., corresponding to a differential radiance of around 0.125 microwatts per centimeter squared, i.e. 2-3 orders of magnitude more sensitive that required to detect the emitted or reflected radiation described in the previous paragraph. Even when additional scattering and spectroscopic filtering losses are considered, these systems should maintain adequate signal-to-noise to image changes in the reflected (or emitted) optical density that occur using on and off-line spectral filtering to distinguish the tagged area. These cameras can be configured into a portable (less than 3 pounds) systems that closely resemble standard video cameras, and used to record and process video data in both indoor and outdoor environments.

The detection principle is based upon the fact that in addition to being able to sense differences in temperature between various materials, infrared sensor systems can also be used to detect differences in the radiance from two objects that are at the same temperature but have different absorption properties, or emissivities. Emissivity is defined as the ratio of the radiance emitted by a given object to that of a blackbody at the same temperature. A blackbody is defined as a perfect absorber and emitter of radiation and therefore has an emissivity of 1.0 and a reflectivity of 0.0. Consequently, emissivity can also be related to the absorptance, or 1-reflectance, of an object.

In another embodiment, an imaging FTIR or hyperspectral sensor could be used for detection.

The radiation emitted from an object at a given temperature (T) and wavelength (λ) can be obtained from Planck's Law:

$$W(\lambda,T)=\epsilon C_1\lambda^{-5}[\exp(C_2/\lambda T)-1]^{-1} \text{ (watts/m}^2/sr/\mu\text{m)}$$

Where W(λ,T)=spectral emittance at wavelength λ for an object at absolute temperature, T (K);

ϵ=emissivity and is equal to 1 for a blackbody $C_1=2\pi hc^2$ $C_2=ch/k$ h=Planck's constant c=speed of light k=Boltzmann's constant In addition to the radiation emitted from the tag and the object to which it is attached, radiant energy emitted from other sources, such as the sun or night sky, may also illuminate the tag and substrate and a portion of this radiation may be reflected into the infrared camera. This contribution to the detected radiance is calculated from Planck's Law in some embodiments. In particular, the spectral distribution of the sun's energy at the surface of the earth is approximated by a blackbody source with a temperature of 6000 K. In either case, the change in the emissivity generated by the absorptance and/or reflectance properties of the tag and the background against which it is viewed spatially modulates the radiance imaged by the infrared sensor, thereby generating the detection signature.

In some embodiments, the detection device used is an infrared camera. For example, in some embodiments, the camera used is a Merlin MID Model Infrared Camera (Indigo Systems Corporation, Goleta, Calif.). Other detection devices could be employed. The camera has an indium antimonide focal plane array with a spectral response in the desired 3-5 μm region of the electromagnetic spectrum, containing the fundamental absorption bands of the deuterated materials. The camera is equipped with, for example, 100-mm and 25-mm lenses. In some embodiments, the camera is also equipped with a removable filter holder that allows spectral filters to be installed after the lens and just in front of the focal plane array. In some embodiments, a spectral filter in the desired range (depending on the material selected, e.g., 3 to 5 μm range) is installed. Such filters are available, for example, from Spectragon, Inc.

In some embodiments, in-band, out-of-band spectral processing is also used to further highlight the presence of the deuterated materials. In this technique, one image is collected using a spectral bandpass (i.e. 4.5 to 5.0 micron) filter containing the deuterated absorption bands and a second image is collected in a spectral region (i.e. 3.8 to 4.2 microns) containing little absorption from the deuterated materials. The two images are then correlated (subtracted and/or divided) to correct for and reduce background contributions.

Figure 12:
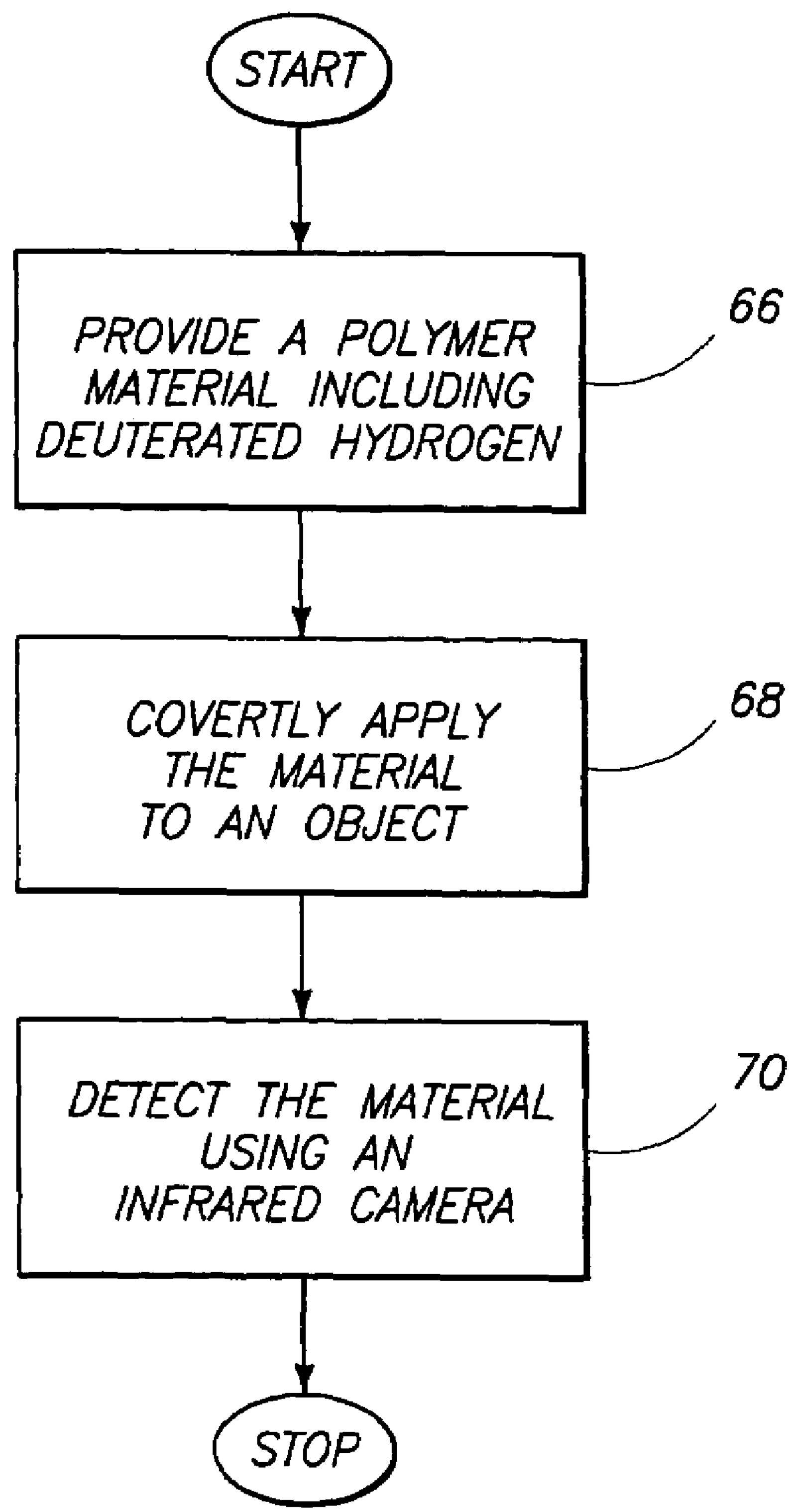
FIG. 12 is a flowchart of a method of covertly tagging and tracking.
Figure 13:
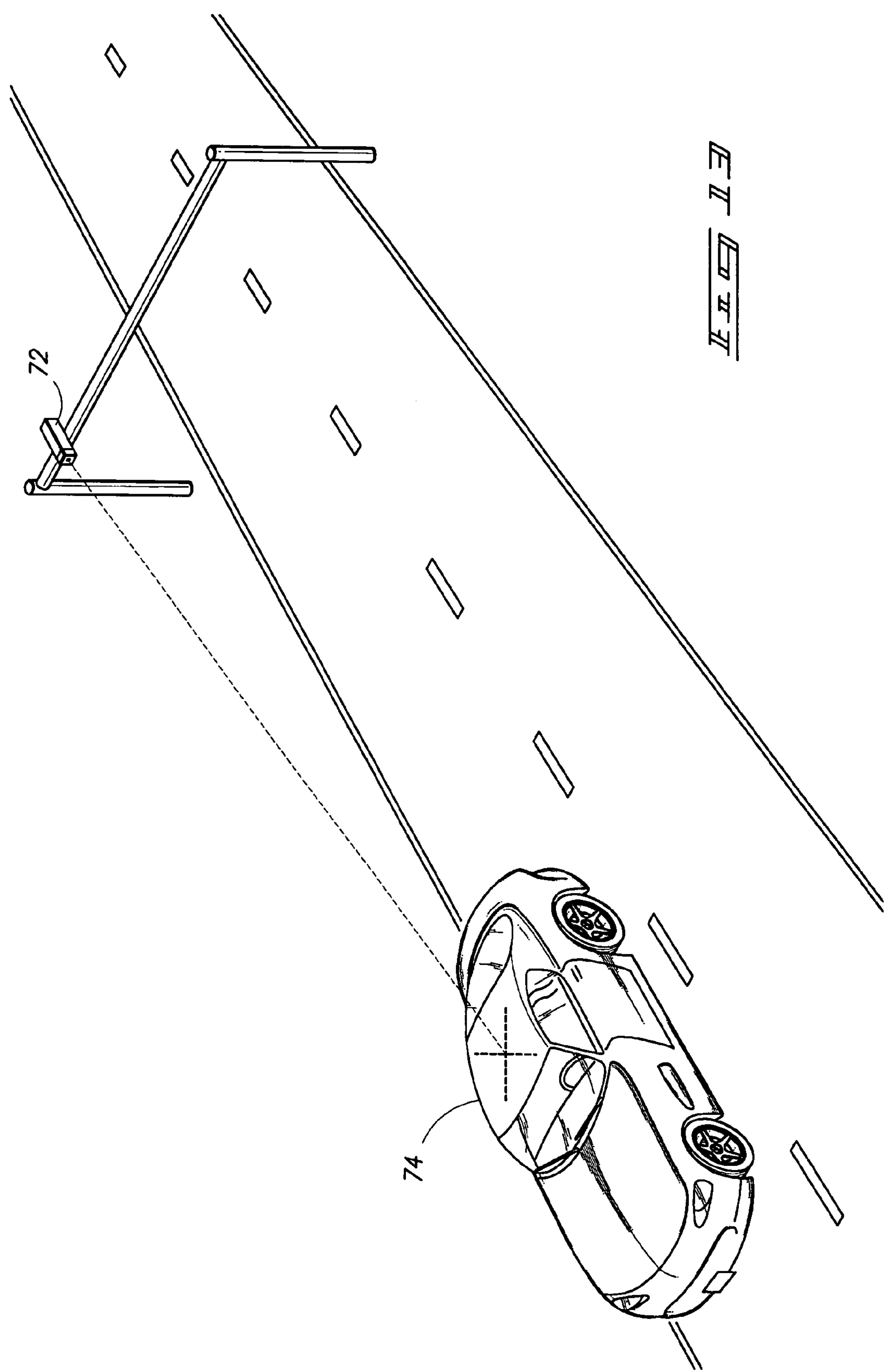
FIG. 13 is a perspective view showing an object being tracked.

FIG. 12 is a flowchart of a method of covertly tagging and tracking, in accordance with various embodiments of the invention. In step 66, a polymer material is provided including deuterated hydrogen. In step 68, the material is covertly applied to an object. In step 70, the material is detected using an infrared camera. FIG. 13 illustrates covertly tracking an object 74 using an infrared camera 72.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of covertly tagging and tracking an object, the method comprising:
- providing a material capable of at least one of being applied to the object and being included in the object, which material includes deuterium;
- performing at least one of applying the material to the object and including the material in the object in a manner in which in the appearance of the object is not changed, to the naked eye; and
- using an infrared camera that is not a microscope, to detect the material from a distance.

2. A method in accordance with claim 1 wherein the material is a coating material.

3. A method in accordance with claim 1 wherein the material comprises wax.

4. A method in accordance with claim 1 wherein the material comprises paint.

5. A method in accordance with claim 1 wherein the material is included in the object when the object is constructed.

6. A method in accordance with claim 1 wherein the material is a polymer.

7. A method in accordance with claim 1 wherein the material comprises plastic.

8. A method in accordance with claim 1 wherein the material is sprayed onto the object.

9. A method of covertly tagging and tracking an object, the method comprising:
- providing a polymer including deuterated hydrogen in a material capable of at least one of being applied to the object and being included in the object;
- performing at least one of applying the material to the object and including the material in the object, wherein the appearance of the object is not changed, to the naked eye; and
- detecting the material from a distance using an infrared camera that is not a microscope.

10. A method in accordance with claim 9 wherein the detection device is an infrared camera.

11. A method in accordance with claim 10 and further comprising storing an image of the object obtained using the camera.

12. A method in accordance with claim 9 wherein the material is a liquid and is sprayed onto the object.

13. A method in accordance with claim 9 wherein the material is painted onto at least a portion of the object.

14. A method in accordance with claim 9 wherein the material is a deuterated polyethylene.

15. A method in accordance with claim 9 wherein the material is a deuterated polystyrene.

16. A method in accordance with claim 9 wherein the material is a deuterated poly(methyl methacrylate).

17. A method in accordance with claim 9 wherein the material is a deuterated poly(ethylene oxide).

18. A method in accordance with claim 9 wherein the material is a deuterated polybutadiene.

19. A method in accordance with claim 9 wherein the material is a deuterated poly(styrene-co-butadiene).

20. A method in accordance with claim 9 wherein the material is a deuterated dotriacontane.

21. A method in accordance with claim 9 wherein the material is a deuterated hexatriacontane.

22. A method of covertly tagging and tracking an object, the method comprising:
- providing a deuterated hydrogen polymer in a material capable of at least one of being applied to the object and being included in the object;
- performing at least one of applying the material to the object and including the material in the object, wherein the appearance of the object is not changed from what was expected, to the naked eye, wherein the material is applied to or included in the object in a predetermined shape, and wherein the material is applied to another object in a different predetermined shape, wherein one object can be distinguished from another object even though the same material is used for both; and detecting the material from a distance using an infrared camera.

23. A method in accordance with claim 22 wherein the material is included in a liquid solution in which the material remains after liquid solvent evaporates, and wherein the liquid solution is sprayed onto the object.

24. A method in accordance with claim 22 wherein the material is a liquid and is sprayed onto the object.

25. A method in accordance with claim 22 wherein the material is painted onto the object.

26. A method of covertly tagging and tracking an object, the method comprising:

substituting deuterium for hydrogen in a polymer material capable of at least one of being applied to the object and being included in the object;

performing at least one of applying the resulting material to the object and including the resulting material in the object wherein the appearance of the object is not changed to the naked eye;

using an infrared camera that is not a microscope, to detect the resulting material from a distance.

27. A method in accordance with claim 26 and further comprising tracking the object using an infrared detector.

28. A method of covertly tagging and tracking an object, the method comprising:

substituting deuterium for hydrogen in an alcohol material capable of being applied to the object; and applying the resulting material to the object such that the appearance of the object is not changed from its appearance without the material, to the naked eye; and using an infrared camera that is not a microscope to detect the object from a large distance.

29. A method in accordance with claim 28 wherein the alcohol material is a polyvinyl alcohol.

30. A method of covertly tagging and tracking an object, the method comprising:

providing an isotope of a material typically applied to or included in the object;

applying the isotope to the object or including the isotope in the object such that the appearance of the object is not changed from its appearance without the material, to the naked eye; and covertly detecting the object with an infrared camera that is not a microscope from a large distance.

31. A method in accordance with claim 30 and further comprising detecting the isotope with an infrared camera.

* * * * *